(12) United States Patent
Han et al.

(10) Patent No.: US 10,989,701 B2
(45) Date of Patent: Apr. 27, 2021

(54) METHOD OF PREDICTING NITROGEN DIOXIDE EMISSION FROM ENGINE

(71) Applicants: Hyundai Motor Company, Seoul (KR); Kia Motors Corporation, Seoul (KR); Seoul National University R&DB Foundation, Seoul (KR)

(72) Inventors: Kyoung-Chan Han, Gunpo-si (KR); Jun-Yong Lee, Seongnam-si (KR); Jun Yu, Suwon-si (KR); Kyoung-Min Lee, Hwaseong-si (KR); Kyoung-Doug Min, Seoul (KR); Seung-Ha Lee, Gwacheon-si (KR); Young-Bok Lee, Incheon (KR)

(73) Assignees: Hyundai Motor Company, Seoul (KR); Kia Motors Corporation, Seoul (KR); Seoul National University R & DB Foundation, Seoul (KR)

( * ) Notice: Subject to any disclaimer, the term of this patent is extended or adjusted under 35 U.S.C. 154(b) by 433 days.

(21) Appl. No.: 16/020,633

(22) Filed: Jun. 27, 2018

(65) Prior Publication Data
US 2019/0162710 A1 May 30, 2019

(30) Foreign Application Priority Data

Nov. 30, 2017 (KR) ........................ 10-2017-0163044

(51) Int. Cl.
*G01N 33/00* (2006.01)
*G01M 15/10* (2006.01)
*G07C 5/08* (2006.01)

(52) U.S. Cl.
CPC ...... *G01N 33/0037* (2013.01); *G01M 15/102* (2013.01); *G07C 5/0808* (2013.01)

(58) Field of Classification Search
None
See application file for complete search history.

(56) References Cited

U.S. PATENT DOCUMENTS

| 7,383,118 B2 | 6/2008 | Imai et al. |
| 2015/0231565 A1* | 8/2015 | Wittrock ................. F01N 3/103 423/212 |
| 2015/0275722 A1* | 10/2015 | Doering ................ F01N 3/0842 60/274 |

FOREIGN PATENT DOCUMENTS

| CN | 1429415 | * | 7/2003 | ............ H01M 8/186 |
| CN | 1719103 | * | 4/2010 | .............. F23C 6/047 |

(Continued)

*Primary Examiner* — Tung S Lau
(74) *Attorney, Agent, or Firm* — Morgan, Lewis & Bockius LLP

(57) ABSTRACT

A method of predicting nitrogen dioxide emission from an engine may include an initial nitrogen dioxide formation prediction operation of predicting an amount of nitrogen dioxide which is originally formed in the engine using a nitrogen dioxide formation model by an electronic control unit (ECU) while engine combustion is underway, a nitrogen dioxide reduction prediction operation of determining an amount of nitrogen dioxide which is reduced to nitrogen monoxide using a reverse reaction of the nitrogen dioxide formation model by the ECU based on the amount of formed nitrogen dioxide in the initial nitrogen dioxide formation prediction operation, and a final nitrogen dioxide emission determination operation of determining an amount of nitrogen dioxide which is ultimately generated by the engine by the ECU based on a difference between the amount of formed nitrogen dioxide and the amount of reduced nitrogen dioxide.

17 Claims, 2 Drawing Sheets

(56) References Cited

FOREIGN PATENT DOCUMENTS

| | | | | |
|---|---|---|---|---|
| CN | 102312704 | * | 1/2012 | ............ F01N 11/002 |
| CN | 101513592 | * | 11/2013 | ............... F01N 3/28 |
| CN | 103573362 | * | 2/2014 | ............. F01N 3/023 |
| CN | 102287253 | * | 7/2014 | ............. F01N 3/208 |
| CN | 109356690 | * | 2/2019 | ........... F01N 3/0222 |
| JP | 2007-127004 A | | 5/2007 | |
| JP | 2010-242728 A | | 10/2010 | |
| JP | 2013-224613 A | | 10/2013 | |
| KR | 10-1317410 B1 | | 10/2013 | |
| WO | WO 2015/130218 | * | 9/2015 | ............. F01N 3/208 |

* cited by examiner

METHOD OF PREDICTING NITROGEN DIOXIDE EMISSION FROM ENGINE

CROSS-REFERENCE TO RELATED APPLICATIONS

The present application claims priority to Korean Patent Application No. 10-2017-0163044, filed on Nov. 30, 2017, the entire contents of which is incorporated herein for all purposes by this reference.

BACKGROUND OF THE INVENTION

Field of the Invention

The present invention relates to a method of predicting nitrogen dioxide emission from an engine, which enables real-time prediction of emission of nitrogen dioxide, among the nitrogen oxides emitted by a vehicle engine, even without an actual detector.

Description of Related Art

Emission limits on various types of harmful materials generated by combustion in an engine mounted in a vehicle have been set forth in regulations, and such regulations are becoming stricter.

To lower the emission of harmful materials from vehicles, the generation of harmful materials at the time of combustion in each cylinder of the engine must be fundamentally decreased.

Also, harmful materials generated from the engine must be converted into harmless materials using a post-treatment device, or collected and then removed.

Harmful materials discharged from vehicles include nitrogen oxides ($NO_x$) including nitrogen monoxide (NO) and nitrogen dioxide ($NO_2$). Nitrogen oxide emission is decreased by controlling the combustion in the cylinder or using a catalyst provided in the post-treatment device. The post-treatment system may include, for example, LNT, SCR or the like, and is provided to achieve the post-treatment of nitrogen oxides to satisfy increasingly stringent regulatory standards.

Meanwhile, a post-treatment device converts a harmful material into a harmless material mainly using a catalyst. Since the catalyst is based on a chemical reaction, to increase the efficiency of the post-treatment device, there is a need to classify the amounts of nitrogen monoxide and nitrogen dioxide that are generated, among nitrogen oxides.

For instance, the purification of nitrogen monoxide and nitrogen dioxide is conducted using SCR as represented by <Reaction Scheme-1>~<Reaction Scheme-3> below.

<Reaction Scheme-1>

<Reaction Scheme-2>

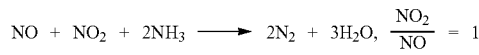

<Reaction Scheme-3>

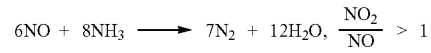

<Reaction Scheme-1> is the scheme of a standard SCR reaction, <Reaction Scheme-2> is the scheme of a high-speed SCR reaction, and <Reaction Scheme-3> is the scheme of a low-speed SCR reaction.

As represented above, depending on the ratio of nitrogen monoxide and nitrogen dioxide in nitrogen oxides, the rate of reduction of nitrogen oxides becomes different, and the amount of ammonia ($NH_3$) which is used may also vary.

However, among nitrogen oxides generated by combustion in the engine, nitrogen dioxide ($NO_2$) is not easy to measure using an additional detector, and therefore it is necessary to determine the magnitude of emission of nitrogen dioxide ($NO_2$), among nitrogen oxides.

The information disclosed in this Background of the Invention section is only for enhancement of understanding of the general background of the invention and may not be taken as an acknowledgement or any form of suggestion that this information forms the prior art already known to a person skilled in the art.

BRIEF SUMMARY

Various aspects of the present invention are directed to providing a method of predicting nitrogen dioxide emission from an engine, which is configured for predicting the amount of nitrogen dioxide among nitrogen oxides emitted from an engine mounted in a vehicle, even without the use of an actual detector.

Other various aspects of the present invention can be understood by the following description, and will become apparent with reference to the exemplary embodiments of the present invention. Also, it will be obvious to those skilled in the art to which the present invention pertains that the objects and advantages of the present invention can be realized by the means as claimed and combinations thereof.

In accordance with various exemplary embodiments of the present invention, there is provided a method of predicting nitrogen dioxide emission from an engine, suitable for predicting the amount of nitrogen dioxide among nitrogen oxides emitted from an engine, the method including: an initial nitrogen dioxide formation prediction operation of predicting the amount of nitrogen dioxide which is originally formed in the engine using a nitrogen dioxide formation model while engine combustion is underway, a nitrogen dioxide reduction prediction operation of determining the amount of nitrogen dioxide which is reduced to nitrogen monoxide based on the amount of formed nitrogen dioxide in the initial nitrogen dioxide formation prediction operation, and a final nitrogen dioxide emission determination operation of determining the amount of nitrogen dioxide which is ultimately generated by the engine based on the difference between the amount of formed nitrogen dioxide and the amount of reduced nitrogen dioxide.

The method of predicting nitrogen dioxide emission from an engine according to an exemplary embodiment of the present invention can predict nitrogen dioxide ($NO_2$) emission in real time among nitrogen oxides ($NO_x$) generated inside the engine, even without providing an actual detector, precisely controlling the amount of material which is additionally injected in a post-treatment device and the reaction rate.

Accordingly, the efficiency of the post-treatment device can increase, decreasing the amount of nitrogen oxides in exhaust gas ultimately emitted from vehicles.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1:
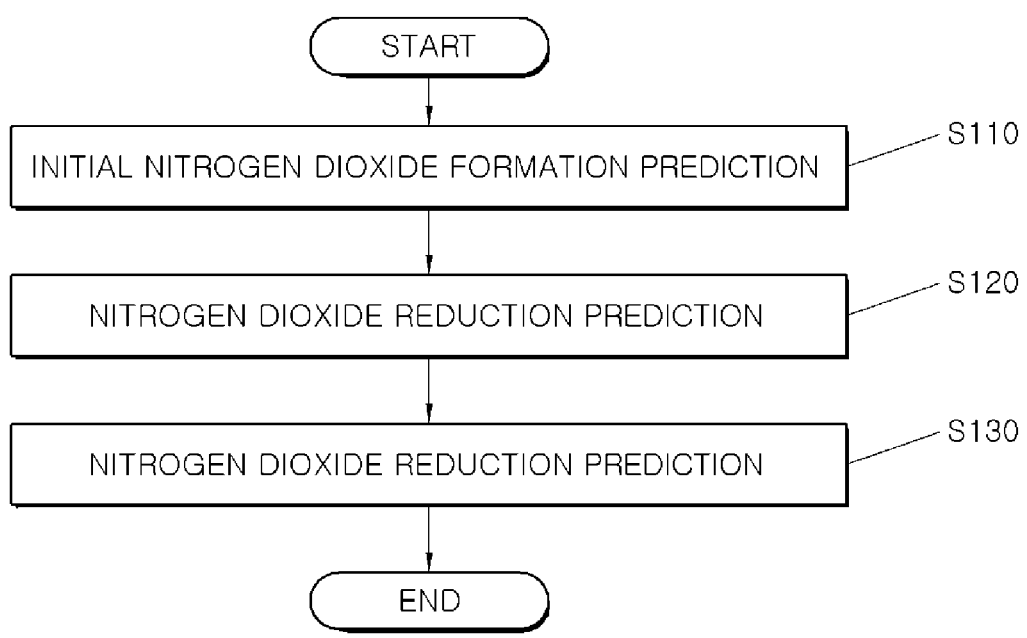
FIG. 1 is a flowchart showing a process of predicting nitrogen dioxide emission from an engine according to an exemplary embodiment of the present invention.

It may be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particularly intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Exemplary embodiments of the present invention will be described below in more detail with reference to the accompanying drawings to be easily realized by those skilled in the art.

The present invention may, however, be embodied in different forms and should not be construed as limited to the exemplary embodiments set forth herein. In various exemplary embodiments, elements irrelevant to the present invention may be omitted in order to avoid obscuring appreciation of the disclosure. Throughout the disclosure, like reference numerals refer to like parts throughout the various figures and embodiments of the present invention.

The drawings are not necessarily to scale, and in some instances, proportions may have been exaggerated to clearly illustrate various layers and regions of the embodiments. It will be understood that when an element including a layer, a film, a region, or a plate is referred to as being "above" another element, it can be "immediately above" the other element, or intervening elements may also be present.

In contrast, when an element is referred to as being "immediately above" another element, there are no intervening elements present. Furthermore, it will be understood that when an element is referred to as being "entirely" formed on another element, it can be formed on the entire surface (or whole surface) of the other element or may not be formed at a portion of the edge thereof.

Hereinafter, a detailed description will be provided of a method of predicting nitrogen dioxide emission from an engine according to embodiments of the present invention with reference to the accompanying drawings.

According to an exemplary embodiment of the present invention, a method of predicting nitrogen dioxide emission from an engine, suitable for predicting the amount of nitrogen dioxide ($NO_2$) among nitrogen oxides ($NO_x$) emitted from an engine, includes an initial nitrogen dioxide formation prediction step (S110) of predicting the amount of nitrogen dioxide ($NO_{2,formation}$) which is originally formed in the engine using a nitrogen dioxide ($NO_2$) formation model while engine combustion is underway, a nitrogen dioxide reduction prediction step (S120) of determining the amount of nitrogen dioxide ($NO_2$) ($NO_{2,decomposition}$) which is reduced to nitrogen monoxide based on the amount of formed nitrogen dioxide ($NO_{2,formation}$) in the initial nitrogen dioxide formation prediction step (S110), and a final nitrogen dioxide emission determination step (S130) of determining the amount of nitrogen dioxide which is ultimately generated by the engine based on the difference between the amount of formed nitrogen dioxide ($NO_{2,formation}$) and the amount of reduced nitrogen dioxide ($NO_{2,decomposition}$).

The method of the invention is performed using a control device, for example, an electronic control unit (ECU), configured to control the engine using the measured values that are input from detectors mounted to the engine. The ECU is configured such that a series of procedures to be described later are preliminarily stored as logic for implementation of each of the processing steps, predicting the amount of nitrogen dioxide ($NO_{2,formation}$) which is originally formed due to combustion in the engine, predicting the amount of nitrogen dioxide ($NO_{2,decomposition}$) which is reduced in the engine, and then predicting the amount of nitrogen dioxide ($NO_{2,out}$) which is emitted from the engine based on the difference between the amount of formed nitrogen dioxide ($NO_{2,formation}$) and the amount of reduced nitrogen dioxide ($NO_{2,decomposition}$).

Accordingly, the amount of nitrogen dioxide ($NO_{2,formation}$) which is originally formed due to combustion in the engine is predicted in the initial nitrogen dioxide formation prediction step (S110), and the amount of reduced nitrogen dioxide ($NO_{2,decomposition}$) is predicted in the nitrogen dioxide reduction prediction step (S120), after which the amount of nitrogen dioxide ($NO_{2,out}$) which is emitted from the engine may be predicted based on the difference between the amount of formed nitrogen dioxide ($NO_{2,formation}$) and the amount of reduced nitrogen dioxide ($NO_{2,decomposition}$).

In the present way, real-time prediction of nitrogen dioxide emission using a detector which is already mounted to the engine becomes possible, without the demand for an additional detector for detecting nitrogen dioxide emission.

In the initial nitrogen dioxide formation prediction step (S110), the amount of nitrogen dioxide which is originally formed in the engine is predicted using the nitrogen dioxide formation model at the time of combustion in the engine.

The nitrogen dioxide formation model may be any one of the following Reaction Schemes.

$NO + HO_2 \leftrightarrow NO_2 + OH$            <Reaction Scheme-4>

$NO + O_2 \leftrightarrow NO_2 + O$            <Reaction Scheme-5>

$2NO + O_2 \leftrightarrow 2NO_2$            <Reaction Scheme-6>

$NO + OH \leftrightarrow NO_2 + H$            <Reaction Scheme-7>

When combustion progresses in the engine, as shown in <Reaction Scheme-4>~<Reaction Scheme-7>, nitrogen monoxide (NO) is formed into nitrogen dioxide ($NO_2$), and a portion thereof undergoes the reverse reaction and thus nitrogen dioxide ($NO_2$) is reduced to nitrogen monoxide (NO). Here, the reaction is mainly conducted using <Reaction Scheme-4>.

The amount of formed nitrogen monoxide (NO) may be predicted using a variety of engine operating parameters, or may be determined using a value which is actually measured using a detector.

In <Reaction Scheme-4>~<Reaction Scheme-7>, formation of nitrogen dioxide ($NO_2$) proceeds based on the amount of formed nitrogen monoxide (NO), which may be affected by temperature, oxygen concentration, nitrogen monoxide concentration, and individual radicals.

The amount of formed nitrogen dioxide ($NO_{2,formation}$) in the initial nitrogen dioxide formation prediction step (S110) may be determined based on the following <Equation-1>.

$$NO_{2,formation} = A \times NO_Q \times \exp\left(\frac{B}{T}\right) \quad \langle\text{Equation-1}\rangle$$

In <Equation-1>, A and B are constants, $NO_Q$ is the amount of nitrogen monoxide in the engine, and T is the in-cylinder temperature.

Here, the constant B may be replaced by $E_A$. $E_A$, which indicates activation energy, may be applied in a form of a parameter related to the chemical reaction in which nitrogen monoxide is converted into nitrogen dioxide depending on the temperature or in a form of a reaction coefficient of the empirical formula, and is determined based on the results of repeated experimentation.

Accordingly, a variety of engine operating parameters related to the formation of nitrogen dioxide may be applied to the above <Equation-1>.

The in-cylinder temperature may be either of the single flame temperature and the highest in-cylinder temperature. Alternatively, the in-cylinder temperature may be a predetermined temperature depending on the fuel-to-oxygen ratio immediately before main injection.

Meanwhile, in the initial nitrogen dioxide formation prediction step (S110), the amount of formed nitrogen dioxide ($NO_{2,formation}$) may be predicted taking into consideration an effect of the engine operating parameter on each of the radicals.

For example, an $HO_2$ radical may be determined from the fuel amount and the intake air amount based on the following <Equation-2>.

(Fuel amount)$^C$×(Oxygen concentration of cylinder)$^D$ <Equation-2>

In <Equation-2>, C and D are constants.

Also, each of the radicals may be predicted by the logic stored in the ECU using the fuel amount, lambda (λ), oxygen amount, intake air amount, EGR, engine speed (RPM), and engine combustion pressure, which are measured using the detectors mounted to a vehicle or an engine, and at least one of the engine operating parameters may be additionally applied to the above <Equation-1>.

For example, the amount of formed nitrogen dioxide ($NO_{2,formation}$) in the initial nitrogen dioxide formation prediction step (S110) may be determined using the following <Equation-3>. That is, exponentiation of the fuel amount and exponentiation of the oxygen concentration of the cylinder may be applied as coefficients to the above <Equation-1>.

This is an example in which a radical related to the chemical reaction is applied as an operating parameter to the above <Equation-1>, taking into consideration the fuel amount and the oxygen amount.

$$NO_{2,formation} = A \times NO_Q \times \exp\left(\frac{B}{T}\right) \times Q_{main+post}^C \times Q_{2,Q}^D \quad \langle\text{Equation-3}\rangle$$

In <Equation-3>, A, B, and C are constants, $E_A$ is the activation energy, T is the in-cylinder temperature, $Q_{main+post}$ is the fuel amount, and $O_{2,Q}$ is the oxygen amount. The fuel amount includes the fuel amount used for main injection and fuel injection other than main injection. For example, A, B, and C may be set as follows: A=736.358, B=3855.357, and C=−1.018.

Furthermore, the in-cylinder temperature may be any one of a single flame temperature, a maximum in-cylinder temperature, and a predetermined temperature depending on the fuel-to-oxygen ratio immediately before main injection, as in the above <Equation-1>.

In the nitrogen dioxide reduction prediction step (S120), the amount of nitrogen dioxide ($NO_{2,decomposition}$) which is reduced to nitrogen monoxide is determined based on the amount of formed nitrogen dioxide ($NO_{2,formation}$) in the initial nitrogen dioxide formation prediction step (S110), predicting the amount of reduced nitrogen dioxide ($NO_{2,decomposition}$).

In the nitrogen dioxide reduction prediction step (S120), the amount of reduced nitrogen dioxide ($NO_{2,decomposition}$) is predicted using the reverse reaction of the nitrogen dioxide ($NO_2$) formation model, and through the reverse reaction of at least one of <Reaction Scheme-4>~<Reaction Scheme-7>, the amount of reduced nitrogen dioxide ($NO_{2,decomposition}$) is predicted.

Here, the amount of reduced nitrogen dioxide ($NO_{2,decomposition}$) is determined based on the following <Equation-4>.

$$NO_{2,decompositon} = NO_{2,formation} \times E \times \exp\left(\frac{F}{T}\right) \quad \langle\text{Equation-4}\rangle$$

In <Equation-4>, E and F are constants, and T is the in-cylinder temperature. The in-cylinder temperature may be any one of a single flame temperature, a maximum in-cylinder temperature, and a predetermined temperature depending on the fuel-to-oxygen ratio immediately before main injection.

The constant F may be replaced by the activation energy, which may be applied in a form of a parameter related to the chemical reaction in which nitrogen dioxide is converted into nitrogen monoxide depending on the temperature or in a form of a reaction coefficient of the empirical formula, and is determined based on the results of repeated experimentation.

In the nitrogen dioxide reduction prediction step (S120), the amount of reduced nitrogen dioxide ($NO_{2,decomposition}$) may be predicted taking into consideration an effect of the engine operating parameter on each of the radicals.

For example, an $HO_2$ radical may be determined from the fuel amount and the intake air amount based on the following <Equation-5>.

(Fuel amount)$^G$×(Oxygen concentration of cylinder)$^H$ <Equation-5>

In <Equation-5>, G and H are constants.

The exponentiation of the fuel amount and the exponentiation of oxygen concentration of the cylinder may be applied as coefficients to <Equation-4>.

Also, in the nitrogen dioxide reduction prediction step (S120), the in-cylinder environmental factor is applied to the above <Equation-4>. Here, the in-cylinder environmental factor is set in consideration of whether the engine is in a compression section or in an expansion section, or may consider an ambient dilution state of a combustion product. That is, when considering the ambient dilution state of the combustion product, at least one of the speed, the swirl ratio, the rail pressure, the injection timing, and the specific time of the engine may be selected and applied. Accordingly, the specific time may be set to any time between the time intervals at which combustion proceeds from the start of combustion to the specific position d. For example, the specific time may be an MFB 40-80 region (Mass Fraction Burn, 40%~80%).

The above is also affected by the temperature, oxygen concentration, nitrogen monoxide concentration, and individual radicals.

Thus, taking into consideration an effect of the engine operating parameter on each of the radicals and the in-cylinder environmental factor in the above <Equation-4>, the amount of reduced nitrogen dioxide ($NO_{2,decomposition}$) may be determined using the following <Equation-6>.

$$NO_{2,decomposition} = NO_{2,formation} \times E \times \exp\left(\frac{F}{T}\right) \times Q_{main+post}^{G} \times Q_{2,O}^{H} \times Speed^{I} \times MI_{[CA]}^{J} \quad \text{<Equation-6>}$$

In <Equation-6>, E, F, G, H, I, and J are constants, T is the in-cylinder temperature, $Q_{main+post}$ is the fuel amount, $O_{2,Q}$ is the oxygen amount, Speed is the engine speed, and $MI_{[CA]}$ is the crank angle upon main injection. The in-cylinder temperature may be any one of a single flame temperature, a maximum in-cylinder temperature, and a predetermined temperature depending on the fuel-to-oxygen ratio immediately before main injection. Here, E=3.721, F=−219.982, G=0.004, H=0.006, I=−0.0067, and J=−0.200.

In the final nitrogen dioxide emission determination step (S130), the amount of nitrogen dioxide ($N_{2,out}$) which is emitted from the engine is determined. In the final nitrogen dioxide emission determination step (S130), the difference between the amount of formed nitrogen dioxide ($NO_{2,formation}$) in the initial nitrogen dioxide formation prediction step (S110) and the amount of reduced nitrogen dioxide ($NO_{2,decomposition}$) in the nitrogen dioxide reduction prediction step (S120) is determined, whereby the amount of nitrogen dioxide ($N_{2,out}$) which is emitted from the engine may be determined.

The nitrogen dioxide emission is represented as follows.

$$NO_{2,out} = NO_{2,formation} - NO_{2,decomposition} \quad \text{<Equation-7>}$$

As described hereinbefore, the amount of formed nitrogen dioxide ($NO_{2,formation}$), the amount of reduced nitrogen dioxide ($NO_{2,decomposition}$) and the amount of emitted nitrogen dioxide ($N_{2,out}$) are predicted from the values that are controlled for engine combustion and the values that are input to the ECU using the existing detectors mounted to the engine, in lieu of using the additional detector for measuring nitrogen dioxide. Thus, even without the additional use of an actual detector, the ECU is responsible for real-time prediction in which the amount of nitrogen dioxide ($N_{2,out}$) which is predicted to be emitted from the engine is substantially the same as the actual emission. Furthermore, the amount of emitted nitrogen dioxide ($N_{2,out}$) thus predicted may be used to precisely control the catalytic reaction rate and the amount of the additional material (e.g., ammonia) to be injected in the post-treatment device, improving the purification performance of the post-treatment device.

Figure 2:
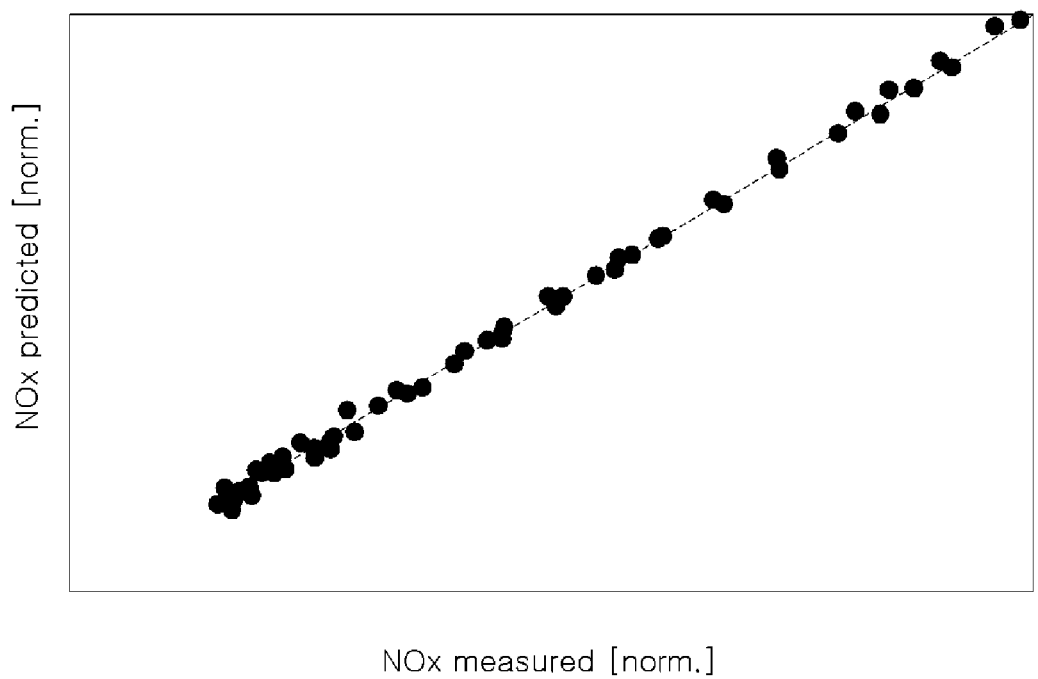
FIG. 2 is a graph showing the predicted results according to the process of the present invention, compared to the actually measured results.

FIG. 2 is a graph showing the results of prediction of nitrogen oxide ($NO_x$) emission from the engine by combining the predicted nitrogen dioxide ($NO_2$) emission according to an exemplary embodiment of the present invention with the measured nitrogen monoxide value.

Accordingly, the predicted emission and the measured emission are substantially identical to each other, and the variance of the predicted emission ($N_{2,out}$) can also be seen to be small.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described to explain certain principles of the invention and their practical application, to enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A method of predicting nitrogen dioxide emission from an engine, for predicting an amount of nitrogen dioxide ($NO_2$) among nitrogen oxides ($NO_x$) emitted from the engine, the method comprising:

an initial nitrogen dioxide formation prediction operation of predicting an amount of nitrogen dioxide which is originally formed in the engine using a nitrogen dioxide formation model by an electronic control unit (ECU) while engine combustion is underway, a nitrogen dioxide reduction prediction operation of determining an amount of nitrogen dioxide which is reduced to nitrogen monoxide using a reverse reaction of the nitrogen dioxide formation model by the ECU based on the amount of formed nitrogen dioxide in the initial nitrogen dioxide formation prediction operation, and a final nitrogen dioxide emission determination operation of determining an amount of nitrogen dioxide which is generated by the engine by the ECU based on a difference between the amount of the formed nitrogen dioxide and the amount of reduced nitrogen dioxide, wherein the amount of the formed nitrogen dioxide in the initial nitrogen dioxide formation prediction operation is determined based on the amount of formed nitrogen monoxide using the following equation:

$$NO_{2,formation} = A \times NO_Q \times \exp\left(\frac{B}{T}\right), \text{ and}$$

wherein $NO_{2,formation}$ is the amount of the formed nitrogen dioxide, A and B are constants, $NO_Q$ is the amount of nitrogen monoxide in the engine, and T is an in-cylinder temperature.

2. The method of claim 1, wherein the amount of the formed nitrogen dioxide in the initial nitrogen dioxide formation prediction operation is determined based on an amount of formed nitrogen monoxide through at least one of the following reaction schemes:

$$NO+HO_2 \leftrightarrow NO_2+OH$$

$$NO+O_2 \leftrightarrow NO_2+O$$

$$2NO+O_2 \leftrightarrow 2NO_2$$

$$NO+OH \leftrightarrow NO_2+H.$$

3. The method of claim 1, wherein the in-cylinder temperature is one of a single flame temperature, a maximum in-cylinder temperature, and a predetermined temperature depending on a fuel-to-oxygen ratio immediately before main injection.

4. The method of claim 1, wherein the amount of the formed nitrogen dioxide in the initial nitrogen dioxide formation prediction operation is predicted using an engine combustion pressure and an engine operating parameter.

5. The method of claim 1, wherein the amount of the reduced nitrogen dioxide in the nitrogen dioxide reduction prediction operation is determined based on the amount of the formed nitrogen dioxide through a reverse reaction of one of the following reaction schemes:

$$NO+HO_2 \leftrightarrow NO_2+OH$$

$$NO+O_2 \leftrightarrow NO_2+O$$

$$2NO+O_2 \leftrightarrow 2NO_2$$

$$NO+OH \leftrightarrow NO_2+H.$$

6. The method of claim 2, wherein the amount of the reduced nitrogen dioxide in the nitrogen dioxide reduction prediction operation is predicted using the following equation:

$$NO_{2,decompositon} = NO_{2,formation} \times E \times \exp\left(\frac{F}{T}\right),$$

wherein $NO_{2,decomposition}$ is the amount of the reduced nitrogen dioxide, E and F are constants and T is an in-cylinder temperature.

7. The method of claim 3, wherein an $HO_2$ radical is determined from a fuel amount and an intake air amount.

8. The method of claim 4, wherein the engine operating parameter includes at least one of a fuel amount, an engine speed (RPM), an air-fuel ratio (AF) and EGR.

9. The method of claim 6, wherein an $HO_2$ radical is determined from a fuel amount and an intake air amount.

10. The method of claim 7, wherein the $HO_2$ radical before formation of nitrogen dioxide is convened and applied based on the following equation:

(Fuel amount)$^C$×(Oxygen concentration of cylinder)$^D$ (wherein C and D are constants).

11. The method of claim 9, wherein the $HO_2$ radical before formation of nitrogen dioxide is converted and applied based on the following equation:

(Fuel amount)$^G$×(Oxygen concentration of cylinder)$^H$ (wherein G and H are constants).

12. The method of claim 10, wherein the amount of the formed nitrogen dioxide in the initial nitrogen dioxide formation prediction operation is determined based on the amount of formed nitrogen monoxide using the following equation:

$$NO_{2,formation} = A \times NO_Q \times \exp\left(\frac{B}{T}\right) \times Q_{main+post}^C \times Q_{2,Q}^D,$$

wherein A, B, C, and D are constants, T is an in-cylinder temperature, $Q_{main+post}$ is a fuel amount, and $O_{2,Q}$ is an oxygen amount.

13. The method of claim 11, wherein the amount of the reduced nitrogen dioxide is determined by applying an in-cylinder environmental factor to the equation of claim 6.

14. The method of claim 11, wherein the amount of the reduced nitrogen dioxide in the nitrogen dioxide reduction prediction operation is predicted using the following equation:

$$NO_{2,decomposition} =$$

$$NO_{2,formation} \times E \times \exp\left(\frac{F}{T}\right) \times Q_{main+post}^G \times Q_{2,Q}^H \times Speed^I \times MI_{[CA]}^J$$

wherein E, F, G, H, I, and J are constants, T is an in-cylinder temperature, $Q_{main+post}$ is a fuel amount, $O_{2,Q}$ is an oxygen amount, Speed is an engine speed, and $MI_{[CA]}$ is a crank angle upon main injection.

15. The method of claim 13, wherein the in-cylinder environmental factor considers whether the engine is in a compression section or in an expansion section, or considers an ambient dilution state of a combustion product.

16. A method of predicting nitrogen dioxide emission from an engine, for predicting an amount of nitrogen dioxide among nitrogen oxides ($NO_x$) emitted from the engine, the method comprising:
an initial nitrogen dioxide formation prediction operation of predicting an amount of nitrogen dioxide which is originally formed in the engine using a nitrogen dioxide formation model by an electronic control unit (ECU) while engine combustion is underway,
a nitrogen dioxide reduction prediction operation of determining an amount of nitrogen dioxide which is reduced to nitrogen monoxide using a reverse reaction of the nitrogen dioxide formation model by the ECU based on the amount of formed nitrogen dioxide in the initial nitrogen dioxide formation prediction operation, and
a final nitrogen dioxide emission determination operation of determining an amount of nitrogen dioxide which is generated by the engine by the ECU based on a difference between the amount of formed nitrogen dioxide and the amount of reduced nitrogen dioxide,
wherein, in the initial nitrogen dioxide formation prediction operation, an engine operating parameter related to formation of nitrogen dioxide is applied to a radical in the nitrogen dioxide formation model by the ECU,
wherein the amount of the formed nitrogen dioxide in the initial nitrogen dioxide formation prediction operation is determined based on an amount of formed nitrogen monoxide using the following equation:

$$NO_{2,formation} = A \times NO_Q \times \exp\left(\frac{B}{T}\right) \times Q_{main+post}^C \times Q_{2,Q}^D, \text{ and}$$

wherein $NO_{2,formation}$ is the amount of the formed nitrogen dioxide, $NO_Q$ is the amount of nitrogen monoxide in the engine, A, B, C, and D are constants, T is an in-cylinder temperature, $Q_{main+post}$ is a fuel amount, and $O_{2,Q}$ is an oxygen amount.

17. A method of predicting nitrogen dioxide emission from an engine, for predicting an amount of nitrogen dioxide among nitrogen oxides ($NO_x$) emitted from the engine, the method comprising:
an initial nitrogen dioxide formation prediction operation of predicting an amount of nitrogen dioxide which is originally formed in the engine using a nitrogen dioxide formation model while engine combustion is underway,
a nitrogen dioxide reduction prediction operation of determining an amount of nitrogen dioxide which is reduced to nitrogen monoxide using a reverse reaction of the nitrogen dioxide formation model based on the amount of formed nitrogen dioxide in the initial nitrogen dioxide formation prediction operation, and
a final nitrogen dioxide emission determination operation of determining an amount of nitrogen dioxide which is generated by the engine based on a difference between the amount of the formed nitrogen dioxide and the amount of reduced nitrogen dioxide,
wherein, in the nitrogen dioxide reduction prediction operation, an engine operating parameter related to reduction of nitrogen dioxide and an ambient dilution state of a combustion product in a cylinder of the engine are applied to a radical in the reverse reaction of the nitrogen dioxide formation model,
wherein the amount of the reduced nitrogen dioxide in the nitrogen dioxide reduction prediction operation is determined based on an amount of reduced nitrogen monoxide using the following equation:

$$NO_{2,decomposition} = NO_{2,formation} \times E \times \exp\left(\frac{F}{T}\right) \times Q_{main+post}^{G} \times Q_{2,Q}^{H} \times Speed^{I} \times MI_{[CA]}^{J}, \text{ and}$$

wherein $NO_{2,decomposition}$ is the amount of the reduced nitrogen dioxide, $NO_{2,formation}$ is the amount of the formed nitrogen dioxide, E, F, G, H, I, and J are constants, T is an in-cylinder temperature, $Q_{main+post}$ is a fuel amount, $O_{2,Q}$ is an oxygen amount, Speed is an engine speed, and $MI_{[CA]}$ is a crank angle upon main injection.

* * * * *